United States Patent [19]

Lindow et al.

[11] Patent Number: 4,634,880
[45] Date of Patent: Jan. 6, 1987

[54] CONFOCAL OPTICAL IMAGING SYSTEM WITH IMPROVED SIGNAL-TO-NOISE RATIO

[75] Inventors: James T. Lindow, Saratoga; Simon D. Bennett; Ian R. Smith, both of Los Gatos, all of Calif.

[73] Assignee: SiScan Systems, Inc., Campbell, Calif.

[21] Appl. No.: 830,964

[22] Filed: Feb. 19, 1986

Related U.S. Application Data

[63] Continuation-in-part of Ser. No. 725,082, Apr. 19, 1982.

[51] Int. Cl.⁴ .................................................. G01N 21/88
[52] U.S. Cl. .................................. 250/566; 350/405
[58] Field of Search ............... 250/566, 572; 350/400, 350/405; 369/110

[56] References Cited

U.S. PATENT DOCUMENTS

3,919,698  11/1975  Bricot et al. .............. 250/566 X
4,139,263  2/1979  Lehureau et al. .............. 350/400

Primary Examiner—Eugene R. LaRoche
Assistant Examiner—Robert J. Pascal
Attorney, Agent, or Firm—Robert S. Kelly

[57] ABSTRACT

A confocal optical imaging system includes a laser for producing a linearly polarized beam which is transmitted through the optical elements of the system, focused on a small spot on the target, and reflected back through the optical elements to a photodetector where the reflectance from the spot is determined. The optical elements include a pinhole plate for restricting the size of the transmitted and reflected beams which plate, along with other of the optical elements, can produce unwanted reflections adding optical noise to the reflected beam from the target. A retardation plate between the pinhole plate and the target alters the polarization of the transmitted beam relative to the reflected beam so that a polarizer will discriminate between the true reflected beam signal and the unwanted reflections to thereby improve the signal-to-noise ratio at the photodetector.

8 Claims, 2 Drawing Figures

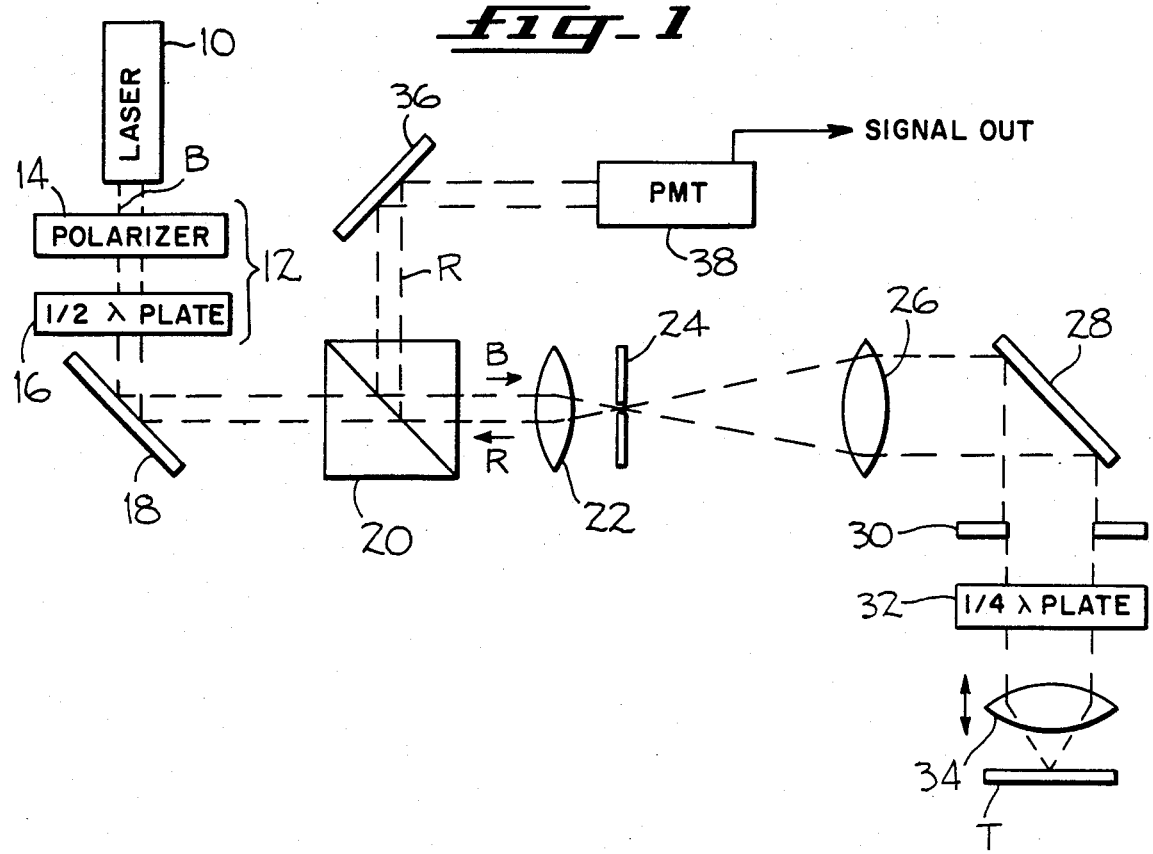
fig_1
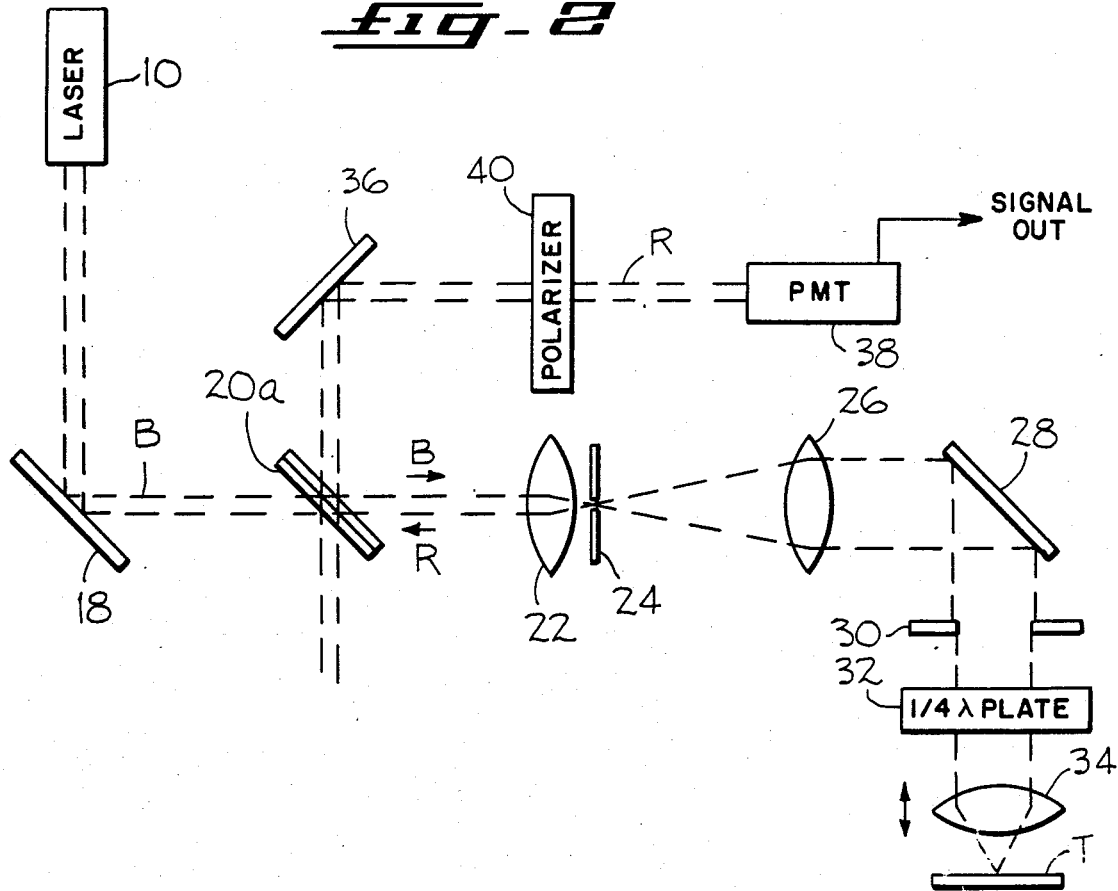
fig_2

CONFOCAL OPTICAL IMAGING SYSTEM WITH IMPROVED SIGNAL-TO-NOISE RATIO

CROSS REFERENCE TO RELATED APPLICATION

This application is a continuation-in-part of U.S. patent application Ser. No. 725,082, filed Apr. 19, 1982, by James T. Lindow et al, and entitled Semiconductor Wafer Scanning System.

BACKGROUND OF THE INVENTION

1. Field of the Invention

The present invention pertains to confocal optical imaging systems wherein a beam of light is passed through a plurality of optical elements and focused on a spot on the target with the reflected beam from the spot being reflected back through the optical elements to a detector, and more particularly, it pertains to such optical imaging systems wherein the transmitted and returned beam are passed through optical elements such as pinhole plates which can provide spurious reflections of the transmitted beam leading to unacceptable noise levels in the output signal.

2. Description of the Prior Act

Recently there has been some considerable interest in optical microscope systems for rapidly scanning specimens, such as semiconductor wafers or the like, at high degrees of resolution. For example, a coherent collimated beam from a laser can be focused on a very tiny spot on the specimen and the reflection from such spot directed back through the optical system to a detector wherein the reflectance can be utilized to inspect or measure various surface features of the specimen such as surface irregularities, profile, line widths, etc. In such a confocal optical system, a pinhole plate and various lenses are used which provide at least partially reflective surfaces which can create spurious signals or optical noise interferring with the reflected or returned beam from the spot on the specimen. Thus, maintaining an adequate signal-to-noise ratio in optical microscope systems of the foregoing type has been a substantial problem.

One general method of dealing with optical noise in a confocal optical system is shown in U.S. Pat. No. 4,139.263 to Lehureau et. al. In this patent there is disclosed an optical system wherein a nonpolarized laser beam is directed through a plurality of optical elements including a beam splitter with such transmitted beam being focused onto a spot on the data carrying target. The return beam from the target passes back through the optical elements and is deflected at the beam splitter to a photodetector. A quarter wave plate is positioned in the path of the beams between the focusing lens and the remainder of the elements in the optical arrangement so as to decouple the incident or transmitted wave from the return or reflected wave thereby reducing the optical noise in the signal received by the photodetector.

Another example of the use of a quarter wave plate in an optical system to reduce optical noise is shown in U.S. Pat. No. 3,919,698 to Bricot et. al.

SUMMARY OF THE INVENTION

With the present invention an improved confocal optical imaging system is provided for directing a coherent beam onto a tiny spot on a target and determining the reflectance therefrom whereby a high signal-to-noise ratio is obtained. The system includes a number of optical elements which receive a linearly polarized light beam and which also direct the reflected beam from the target to a photodetector for providing an electrical output signal. Means are provided for discriminating between the actual reflected signal from the target and the optical noise created by internal reflections from the various optical elements so that the accuracy of the output signal is maintained.

Briefly, the optical system includes a beam splitter for passing at least a portion of the transmitted beam and for receiving and directing at least a portion of the reflected beam from the target to the photodetector. The optical elements, which are positioned between the beam splitter and the target, include a pinhole plate, a lens for contracting the transmitted beam to focus it at the pinhole in the plate, an expansion lens for redirecting the transmitted beam to the target after it has passed through the pinhole, and a focusing lens for focusing the transmitted beam on the target. In order to discriminate between the reflected beam from the target and the internally reflected light beams, a retardation plate is located in the beam path between the pinhole plate and the target for altering the polarization of the transmitted beam relative to the reflected beam, and polarization means is also provided for discriminating in favor of the reflected beam thereby passing only such beam to the photodetector while rejecting those light beams reflected internally from the various optical elements.

BRIEF DESCRIPTION OF THE DRAWING

FIG. 1 is a diagramatic illustration of one embodiment of the optical system of the present invention.

FIG. 2 is a diagramatic illustration of a second embodiment of the optical system of the present invention.

DESCRIPTION OF THE PREFERRED EMBODIMENTS

Referring first to the optical system shown in FIG. 1, a laser source 10 is shown providing a coherent light beam B which is linearly polarized. Alternatively, additional polarizers can be used in the path of the laser to assure a high degree of linear polarization. An isolator assembly 12 comprising a polarizer 14 and a half wave plate 16 is placed in the path of the emitted laser beam B in order to isolate the laser source from internally reflected light beams from the optical elements in the system, as will be explained in greater detail hereinafter.

The light beam B is turned by a mirror 18 and is passed through a polarizing beam splitter 20 comprising a cube oriented so that substantially all of the beam passes straight through the exit and entry faces of the cube without deflection; that is to say, the polarizing beam splitter cube 20 has its exit and entry faces oriented along the axis of the laser beam B so that the beam will pass straight through as shown in FIG. 1. Since the laser beam has already been linearly polarized there will be substantially no deflection of light along an axis at right angles to the entry and exit face axis from the transmitted beam B of the laser source.

A plurality of optical elements are provided in the path of the transmitted laser beam B to permit a return of the reflected beam limited only to the direct collimated rays of the transmitted beam B. Thus, a pinhole lens 22 is provided along with a spatial filter, or pinhole plate, 24 and an expansion lens 26. The pinhole plate 24 has a small pinhole at the focal point of the two lenses 22 and 26 with the pinhole being smaller than the airy disc of the reflected or return beam R, i.e., it will be in the micron diameter range for semiconductor wafer scanning operations such as might be utilized by the present invention. e.g., at a diameter in the order of about 10 microns. It will be seen that the expansion lens 26 recollimates the transmitted beam B so that only substantially parallel rays of light emanate therefrom, such beam having a diameter of about one centimeter.

The transmitted beam B is then turned by a mirror 28 to change its direction to the vertical, and a controlled apperature device 30 is provided to stop down this beam to the desired size. This size will be determined by the amount of area desired to be covered by the focused spot on the underlying target T.

Focusing of the transmitted beam B is provided by an objective lens 34 which is moveable vertically over very small distances (in the micron or submicron range) so as to focus the transmitted beam B on the target T in a very small spot, typically about one micron in diameter. With target T representing a semiconductor wafer for example, scanning of the wafer can be accomplished by moving the wafer in a plane transverse to the projected beam and by making readings of the reflected or return beam R therefrom predetermined time intervals.

As noted, the optical system shown in FIG. 1 is a confocal system so that the reflected beam R from the target T is reflected back through the elements of the system to the beam splitter 20 wherein it will be deflected at right angles to the path of the beam B and directed by a turning mirror 36 to a photomultiplier tube or photodetector 38 providing an electrical output signal that will be dependent upon the amount of light directly reflected from the spot on the surface of the target. An important feature of the present invention is the use of a retardation plate 32 which alters the polarization between the transmitted beam B and the reflected beam R so that these beams can thereafter be differentiated on the basis of their polarization to thereby eliminate the effect of the optical noise created by internal reflections from the optical elements, and particularly, reflections from the pinhole plate 24 which would otherwise directly add optical noise to the signal created by the reflected beam R. The retardation plate 32 comprises a quarter wave length plate which is oriented with its fast axis at 45 degrees to the polarization axis of the transmitted beam B. Thus, the quarter wave length plate acts to circularly polarize the beam B which is transmitted through the focusing leans 34 to the target and to again shift the circularly polarized return beam R to a linearly polarized beam as it passes therethrough. It will be seen, however, that the return beam will be shifted by 90 degrees in polarization from the transmitted beam. Thus, when the return beam strikes the beam splitter cube 20 oriented in polarization as explained previously, substantially all of such beam will be deflected at right angles in the direction shown since this beam R is linearly polarized 90 degrees to the polarization of beam B. However, any internal reflections from the optical elements (obviously having the same or nearly the same state of polarization as the transmitted beam B) will pass straight through the beam splitter cube in and along the path of the transmitted beam B. In order to prevent such spurious beams from interferring with the laser beams generated from source 10, the isolator 12 is provided as shown. While the retardation plate 32 is shown being placed in the beam path just ahead of the focusing lens 34. it will be understood that the plate 32 could be located anywhere it can conveniently be placed downstream of the pinhole plate 24 as, for example, directly downstream of the pinhole plate (i.e., between plate 24 and lens 26) where the smaller beam diameter would use only the center of the retardation plate where it would be subject to the least amount of any possible distortion.

An additional advantage is provided by using a circularly polarized beam at the target in that the orientation of the target will often times discriminate between light of different polarization angles, and a circularly polarized beam will best assure a clean return signal from a target of unknown orientation.

The embodiment of the invention shown in FIG. 2 is similar to the embodiment of the invention shown in FIG. 1 and the same or similar elements are given the same numbers. In the FIG. 2 embodiment, however, a conventional beam splitter 20a is used to divide the transmitted beam B and the return beam R on the basis of a predetermined percentage, e.g., 50%–50%. A separate polarizer plate 40 is then utilized to provide the polarizing means which discriminates between the true reflected or return beam R and spurious light waves created by internal reflections particularly from the face of the pinhole plate 24. Although not absolutely necessary, such a polarizer plate could also be used in the FIG. 1 embodiment to provide further discrimination between the true return signal and any unwanted or spurious signals.

In the FIG. 2 embodiment of the invention, the transmitted beam B will be split at the beam splitter plate 20a with a predetermined percentage passing therethrough and the remaining predetermined percentage being deflected vertically downward as shown. The beam B is then passed through the optical elements of the system including the focusing lens 34 as previously explained, and the return beam R, comprised of the reflected rays from the tiny spot on the target, likewise pass through the optical elements of the system in the reverse direction. It will be seen, therefore, that the rays of light deflected at the beam splitter 20a will be comprised of the reflected beam R which is polarized at 90 degrees to the transmitted beam B through the action of the retardation plate 32 as explained with respect to the FIG. 1 embodiment of the invention. Also, similarly deflected will be the predetermined percentage of the internally reflected rays from the optical elements which, as with the previous embodiment, will be polarized similarly to the transmitted beam B. The polarizer 40 is oriented to transmit substantially all of those beams which are oriented in alignment with the return beam. Thus, the spurious reflections from the optical elements, oriented in accordance with the transmitted beam B, will be substantially entirely rejected by the polarizer 40 and not transmitted to the photomultiplier tube 38 where they might create a spurious output signal. As noted, the optical isolator 12 is not really needed in the FIG. 2 embodiment of the invention and hence has been eliminated.

Although the best modes contemplated for carrying out the present invention have been herein shown and described, it will be apparent that modification and variation may be made without departing from what is regarded to be the subject matter of the invention.

What is claimed is:

1. A confocal optical imaging system with an improved signal-to-noise ratio for directing a coherent beam onto a spot on a target and determining the reflectance therefrom, said system comprising means for producing a linearly polarized light beam; a photodetector for receiving a reflected light beam from the target; a beam splitter for passing at least a portion of the transmitted beam from the beam producing means to the target and for receiving and directing at least a portion of the reflected beam from the target to the photodetector; a plurality of optical elements positioned between the beam splitter and the target including a pinhole plate, a lens for contracting the transmitted beam to focus it at the pinhole in the plate, an expansion lens for redirecting the transmitted beam to the target after it has passed through the pinhole, and a focusing lens for focusing the transmitted beam on the target; a retardation plate located in the beam path between the pinhole plate and the target for altering the polarization of the transmitted beam relative to the reflected beam; and polarization means for passing only the reflected beam from the target to the photodetector and rejecting those beams reflected from the optical elements between the retardation plate and the beam splitter 2. A confocal optical imaging system according to claim 1 wherein said polarization means comprises a polarizer positioned in the path of the reflected beam so as to discriminate between the reflected beam from the target and beams reflected from said plurality of optical elements.

3. A confocal optical imaging system according to claim 2 wherein said polarizer is positioned in the reflected beam path between the beam splitter and the photodetector.

4. A confocal optical imaging system according to claim 1 wherein said polarization means and said beam splitter comprise a polarizing beam splitter aligned in the path of the beams to pass substantially all of the transmitted beam from the beam producing means and to reflect substantially all of the reflected beam from the target to the photodetector.

5. A confocal optical imaging system according to claim 4 including an isolator positioned in the beam path between the beam producing means and the beam splitter for absorbing reflected beams passed through said beam splitter.

6. A confocal optical imaging system according to claim 1 wherein said retardation plate comprises a one-quarter wavelength plate thereby providing a circularly polarized beam at the target.

7. A confocal optical imaging system according to claim 2 wherein said retardation plate comprises a one-quarter wavelength plate thereby providing a circularly polarized beam at the target.

8. A confocal optical imaging system according to claim 4 wherein said retardation plate comprises a one-quarter wavelength plate thereby providing a circularly polarized beam at the target.

* * * * *